United States Patent [19]

Hunsucker

[11] 4,072,741

[45] Feb. 7, 1978

[54] METHOD OF CONTROLLING THE GROWTH OF BACTERIA AND FUNGI USING N-HYDROXYMETHYLALKYLENE DIAMINES

[75] Inventor: Jerry Hoyt Hunsucker, Terre Haute, Ind.

[73] Assignee: IMC Chemical Group, Inc., Terre Haute, Ind.

[21] Appl. No.: 752,213

[22] Filed: Dec. 17, 1976

[51] Int. Cl.² ............................................. A01N 9/20
[52] U.S. Cl. ...................................................... 424/325
[58] Field of Search ..................... 424/325; 260/584 R

[56] References Cited

U.S. PATENT DOCUMENTS

| | | | |
|---|---|---|---|
| 3,876,704 | 4/1975 | Nakaguchi | 260/584 R |
| 3,965,265 | 6/1976 | Koppensteiner et al. | 424/204 |
| 3,975,443 | 8/1976 | Harper et al. | 260/558 D |

*Primary Examiner*—Leonard Schenkman
*Attorney, Agent, or Firm*—Robert H. Dewey; Howard E. Post

[57] ABSTRACT

A method of controlling the growth of bacteria and fungi by applying to them or to the environment inhabited by them a growth inhibiting amount of an N-hydroxymethylalkylene diamine having an alkylene group of 2 to 4 carbon atoms, or mixtures thereof.

5 Claims, No Drawings

METHOD OF CONTROLLING THE GROWTH OF BACTERIA AND FUNGI USING N-HYDROXYMETHYLALKYLENE DIAMINES

BACKGROUND OF THE INVENTION

This invention relates to a method of controlling the growth of microorganisms. In a particular aspect, this invention relates to a method of controlling the growth of microorganisms by the use of a substituted diamine.

Numerous compounds have been disclosed for controlling the growth of microorganisms such as bacteria and fungi. However, it has long been the experience of workers in this field that the microorganisms, after prolonged exposure to toxic compounds at sub-lethal levels, often develop a resistance to them. Consequently, there is a continuing need for new products useful for controlling the growth of microorganisms.

SUMMARY OF THE INVENTION

It is an object of this invention to provide a method of controlling the growth of microorganisms.

It is another object of this invention to provide a method of controlling the growth of microorganisms using an N-hydroxymethyl-substituted diamine.

Other objects of this invention will be apparent to those skilled in the art from the disclosure herein.

It is the discovery of this invention to provide a method of controlling the growth of microorganisms by applying to them or the environment inhabited by them a growth-inhibiting amount of an N-hydroxymethylalkylene diamine having an alkylene group of from 2 to 4 carbon atoms.

DETAILED DISCUSSION

The compounds useful in the practice of this invention are N-hydroxymethyl derivatives of aliphatic diamines. Compounds having straight carbon chains are preferred, but branched chain compounds are also useful. Accordingly the term alkylene is intended to include groups represented by the formula $-(CH_2)_x-$ as well as groups having the entity

in the chain where R is alkyl. The amine groups can be on adjacent carbon atoms or more widely separated, and the hydroxymethyl group can be on either nitrogen. It is also contemplated that mixtures of these compounds will be employed.

These compounds are relatively easily prepared by reacting the aliphatic diamine with formaldehyde in about a 1:1 mole ratio at elevated temperatures, e.g. from about 60° to 100° C. Water is conveniently used as a solvent for the reaction and is easily stripped when the reaction is complete. After removal of the solvent, the residual product can be used in its impure state, or, if preferred, it can be distilled at reduced pressure.

The aliphatic diamines useful in preparing the compounds of this invention are either commercially available or can be prepared by known methods. It is contemplated that these diamines include but are not necessarily limited to 1,2- diaminoethane; 1,3-diaminopropane, 1,2-diaminopropane; 1,4-diaminobutane; 1,2-diaminobutane; 1,3-diamino-1-methyl- propane; 1,3-diamino-2-methylpropane; and 2,3-diaminobutane.

The formaldehyde used in the practice of this invention can be any convenient source, such as gaseous formaldehyde from a formaldehyde generator, paraformaldehyde, aqueous formaldehyde solutions, or alcoholic, e.g. alcohols of 1-4 carbon atoms, solutions. Generally the aqueous solution or paraformaldehyde will be preferred for reasons of economy.

The compounds useful in the practice of this invention are generally effective to combat the growth of bacteria at low concentrations, e.g. 500 ppm. There is, of course, no upper limit to the amount that can be used but generally they become uneconomical above about 5000 ppm and accordingly a use concentration of 500-5000 ppm is contemplated. Generally, however, a concentration between 1000 and 2000 ppm is preferred.

Most, if not all, of the N-hydroxymethylalkylene diamines are conveniently applied to the environment inhabited by microorganisms as an aqueous solution or dispersion. They are particularly effective in aqueous systems such as starch adhesives and solutions, drilling muds for the petroleum industry and in water-dilutable cutting oils based on petroleum hydrocarbons.

These compounds are also soluble in, e.g., alcohols, ketones and most other organic solvents, including hydrocarbons. Solutions of the water-insoluble compounds in such solvents can be used in substantially non-aqueous or 2-phase systems where desired.

The anti-microbial N-hydroxymethylalkylene diamines of this invention can be used without dilution for the control of a wide variety of organisms. Preferably, however, they are used in a dispersed form in a suitable extending agent.

The method of combatting microoganisms of this invention comprises application of the N-hydroxymethylalkylene diamine to a substratum infested with the microorganisms to be combatted or to a substratum to be protected from infestation with the microorganisms. The term substratum as used herein is intended to mean the environment or medium upon which an organism grows. No attempt has been made to determine if the products actually cause the death of the organism or merely prevent their growth.

The term "dispersed" is used herein in the widest possible sense. When the anti-microbial agents of this invention are said to be dispersed, it can mean that the particles of the anti-microbial agents are molecular in the form of a true solution in a suitable organic solvent. It can also mean that the particles are colloidal in size and distributed throughout a liquid phase in the form of particles held in suspension by wetting agents.

The invention will be better understood with reference to the following examples. It is understood however that the examples are intended only to illustrate the invention and it is not intended that the invention be limited thereby.

EXAMPLE 1

Ethylene diamine 60 g (1 mole) and paraformaldehyde 33 g (1.1 mole as formaldehyde) were mixed in about 100 ml of water. Mixing was accompanied by a strong exotherm which brought the mixture to boiling. It was cooled somewhat until the reaction subsided. It was then heated under reflux at about 78° C for about 90 minutes. Water was then strippd and the product was distilled at 40° C at 28 mm Hg. There was obtained N-hydroxymethylethylene diamine.

The compound was tested for anti-bacterial and anti-fungal activity by determining the minimum inhibitory concentration (MIC) by a known method. The MIC is the range between the highest concentration which permits growth (the lower figure in the table) and the lowest concentration which prevents growth (the higher figure in the table). The ranges increase exponentially. Because of uncontrollable variables, such as the vigor of the organism, the data are reproducible to about plus or minus one range. The results are given in the following table.

| MINIMUM INHIBITORY CONCENTRATION | |
| --- | --- |
| | MIC, ppm |
| BACTERIA | |
| Bacillus subtilis | 500–1000 |
| Staphylococcus aureus | 250–500 |
| Streptococcus fecalis | 250–500 |
| Sarcina lutea | 125–250 |
| Escherichia coli | 250–500 |
| Aerobacter aerogenes | 125–250 |
| Pseudomonas aeruginosa | 250–500 |
| Salmonella typhi | 125–250 |
| Desulforibrio aestuarii | 500–1000 |
| FUNGI | |
| Cladosporium herbarum | 500–1000 |
| Cephalosporium species | 1000–2000 |
| Trichophyton mentagrophytes | 32.25–64.5 |
| Aspergillus niger | >2000 |
| Aureobasidium pullulans | 500–1000 |
| Fusarium moniliforme | >2000 |
| Saecharomyces cerevisiae | 64.5–125 |
| Candida albicans | >2000 |
| A cutting oil emulsion is prepared according to the following formula: | |
| Light mineral oil | 20 parts |
| Water | 76.5 |
| N-Hydroxymethylethylene diamine | 0.5 |
| Mixed $C_{18}$ fatty acids | 3 |
| | 100 |

The emulsion remains free from microbial contamination when used as cutting oil.

EXAMPLE 2

The experiment of Example 1 is repeated in all essential details except that 1,3-propylene diamine is substituted for ethylene diamine. There is obtained N-hydroxymethyl- 1,3-propylene diamine. It is inhibitory to most organisms at a concentration of 1000 ppm.

EXAMPLE 3

The experiment of Example 1 is repeated in all essential details except that 1,4-butylene diamine is substituted for ethylene diamine. There is obtained N-hydroxymethyl-1,4- butylene diamine. It is inhibitory to most organisms at a concentration of 1000 ppm.

EXAMPLE 4

The experiment of Example 1 is repeated in all essential details except that 1,2-diaminopropane is substituted for 1,3-propylene diamine. There is obtained an isomeric mixture of N-hydroxymethyl-1,2-diaminopropanes. It is inhibitory to most organisms at a concentration of 1000 ppm.

EXAMPLE 5

The experiment of Example 1 is repeated in all essential details except that 1,2-diaminobutane is substituted for ethylene diamine. There is obtained an isomeric mixture of N-hydroxymethyl-1,2-diaminobutanes. It is inhibitory to most organisms at a concentration of 1000 ppm.

EXAMPLE 6

The experiment of Example 1 is repeated in all essential details except that 1,3-diamino-1-methylpropane is substituted for ethylene diamine. There is obtained an isomeric mixture of N-hydroxymethyl-1,3-diaminobutanes. It is inhibitory to most microorganisms at a concentration of 1000 ppm or more.

EXAMPLE 7

The experiment of Example 1 is repeated in all essential details except that 2-methyl-1,3-diaminopropane is substituted for ethylene diamine. There is obtained N-hydroxymethyl 2-methyl-1,3-diaminopropane. It is inhibitory to most organisms at a concentration of 1000 ppm or more.

EXAMPLE 8

The experiment of Example 1 is repeated in all essential details except that 2,3-diaminobutane is substituted for ethylene diamine. There is obtained an isomeric mixture of N-hydroxymethyl-2,3-diaminobutanes. It is inhibitory to most organisms at a concentration of 1000 ppm or more.

I claim:

1. A method of controlling the growth of bacteria and fungi comprising applying to them or to the environment inhabited by them a growth-inhibiting amount of an N-hydroxymethylalkylene diamine, the alkylene group having from 2 to 4 carbon atoms, or a mixture thereof.

2. The method of claim 1 wherein the growth-inhibiting amount is 500 ppm or above.

3. The method of claim 1 wherein the diamine is N-hydroxymethyl ethylene diamine.

4. The method of claim 1 wherein the hydroxymethylalkylene diamine contains 4 carbon atoms.

5. The method of claim 1 wherein the hydroxymethylalkylene diamine contains 5 carbon atoms.

* * * * *